US007784465B2

(12) United States Patent
Le et al.

(10) Patent No.: US 7,784,465 B2
(45) Date of Patent: Aug. 31, 2010

(54) LARYNGEAL MASK VENT CLIP AND METHOD OF USE

(75) Inventors: Hongha T. Le, Moraga, CA (US); Chih Hua Wang, Sijhih (TW)

(73) Assignee: Nellcor Puritan Bennett LLC, Boulder, CO (US)

( * ) Notice: Subject to any disclaimer, the term of this patent is extended or adjusted under 35 U.S.C. 154(b) by 1307 days.

(21) Appl. No.: 11/238,094

(22) Filed: Sep. 28, 2005

(65) Prior Publication Data

US 2007/0068532 A1   Mar. 29, 2007

(51) Int. Cl.
*A61M 16/00* (2006.01)
*A61M 29/00* (2006.01)
*A62B 9/06* (2006.01)
*A62B 9/02* (2006.01)
*F16K 35/00* (2006.01)
*F16K 15/00* (2006.01)
*F16K 17/00* (2006.01)
*F16K 21/04* (2006.01)

(52) U.S. Cl. ............................ 128/207.16; 128/207.14; 251/93; 604/99.02; 137/522

(58) Field of Classification Search ............. 128/207.15, 128/207.14, 206.24, 201.28, 205.24, 206.15, 128/207.16, 203.11, 205.19, 200.24, 207.12, 128/206.21, 200.26; 251/83, 90, 91, 92, 251/93; 137/522, 523; 604/99.01, 99.02, 604/99.03, 256; 267/53
See application file for complete search history.

(56) References Cited

U.S. PATENT DOCUMENTS

| 2,361,890 | A | * | 10/1944 | Watson ...................... 137/223 |
| 2,530,899 | A | * | 11/1950 | Mueller ................... 292/307 R |
| 2,591,514 | A | * | 4/1952 | Courtot ....................... 251/297 |
| 2,673,570 | A | * | 3/1954 | Cunningham et al. .. 137/543.13 |
| 2,690,895 | A | * | 10/1954 | Barcus ........................ 251/297 |
| 2,896,971 | A | * | 7/1959 | Kolar ....................... 251/149.7 |
| 3,064,287 | A | * | 11/1962 | Maholm ...................... 441/92 |
| 3,882,760 | A | * | 5/1975 | Pass ............................ 91/422 |
| 4,116,212 | A | * | 9/1978 | Cooper ....................... 137/220 |
| 4,147,170 | A | * | 4/1979 | Taylor ................... 128/207.15 |
| 4,759,349 | A | * | 7/1988 | Betz et al. ...................... 604/27 |
| 5,297,547 | A | * | 3/1994 | Brain ..................... 128/207.15 |
| 5,609,195 | A | * | 3/1997 | Stricklin et al. ............. 141/346 |
| RE35,531 | E | * | 6/1997 | Callaghan et al. ....... 128/207.15 |
| 6,247,620 | B1 | * | 6/2001 | Makainai ................. 222/185.1 |
| 6,422,239 | B1 | * | 7/2002 | Cook ..................... 128/207.15 |
| 2002/0129858 | A1 | * | 9/2002 | Meyer et al. ........... 137/625.48 |

\* cited by examiner

*Primary Examiner*—Justine R Yu
*Assistant Examiner*—Kristen C Matter
(74) *Attorney, Agent, or Firm*—Fletcher Yoder

(57) ABSTRACT

A laryngeal mask includes an airway conduit, and a mask connected to the airway conduit, the mask that includes an inflatable portion. An inflation lumen is coupled to the inflatable portion of the mask as well as an inflation valve. The inflation valve includes an exterior housing that has an exit aperture and a stem that is movable between an open position and a closed position. A vent clip is removably coupled to the inflation valve and includes a body portion, an exterior housing interface portion extending from the body portion and a finger extending from the body portion. The exterior housing interface portion includes a gripping surface which is formed to contact at least an approximately 90 degree portion of the inflation valve exterior housing and the finger maintains the inflation valve in an open position.

27 Claims, 2 Drawing Sheets

LARYNGEAL MASK VENT CLIP AND METHOD OF USE

TECHNICAL FIELD

The present disclosure relates generally to airway devices and more specifically to a laryngeal mask including a vent clip and method of use thereof.

BACKGROUND

Laryngeal masks are used to ventilate and to supply anesthetic gases to a patient during surgery. Laryngeal masks typically include an airway conduit and a mask with and inflatable cuff. After insertion into a subject, the inflatable cuff is inflated with air supplied along an inflation conduit to form a seal around a laryngeal inlet. The inflation conduit terminates in a pilot balloon and inflation valve.

Laryngeal masks may be sterilized using heating and vacuuming processes. Between product packaging and patient use, including during sterilization, it may be desirable to maintain the inflation valve in an open position. This may be accomplished using a vent clip. A currently available vent clip 200, as shown in FIG. 2, utilizes two small gripping surfaces 202 and 204 for gripping portions of the inflation valve to connect the vent clip to the inflation valve. Vent clip 200 utilizes a generally flat projection 206 to hold the stem of the inflation valve in an open position. Currently available vent clips suffer from a number of drawbacks and often become dislodged from the inflation valve during sterilization, transport or handling. For a single use type laryngeal mask, the entire laryngeal mask may no longer be suitable for use if the vent clip has become inadvertently dislodged prior to use.

SUMMARY

Therefore a need has arisen for an improved laryngeal mask inflation valve vent clip that will remain attached to an inflation valve until the laryngeal mask is ready for use. A further need has arisen for a laryngeal mask inflation valve vent clip which has an intuitive design.

According to one specific example embodiment, a laryngeal mask includes an airway conduit and a mask connected to the airway conduit that includes an inflatable portion. An inflation conduit may be connected with the inflatable portion of the mask and to an inflation valve. The inflation valve may include an exterior housing with an exit aperture and a stem that is movable between an open position and a closed position. A vent clip may be removably coupled to the inflation valve and may include a body portion, an exterior housing interface portion extending from the body portion, and a finger extending from the body portion. The exterior housing interface portion may include a gripping surface that may be formed to contact a portion, e.g., at least an approximately 90 degree portion, of the inflation valve exterior housing. The finger may be appropriately sized to engage the movable stem of the inflation valve.

According to another specific example embodiment, a vent clip for use with an inflation valve of a laryngeal mask is disclosed. The vent clip may include a body portion, an exterior housing interface portion extending from body portion and a finger extending from the body portion. The exterior housing interface portion may include a gripping surface formed to contact a portion, e.g., at least an approximately 90 degree portion, of an exterior surface of an exterior housing of an inflation valve. The finger may be sized to engage a movable stem of an inflation valve.

According to another specific example embodiment, a method is disclosed for providing a vent clip for a mask having an inflatable portion. The method may include providing a vent clip body portion and forming an exterior housing interface portion extending from the vent clip body portion. The exterior housing interface portion may include a gripping surface that may be formed to contact a portion, e.g., at least an approximately 90 degree portion of the exterior surface of an exterior housing of a laryngeal seal mask inflation valve. The method may also include forming a finger extending from the body portion that may be sized, e.g., to engage a movable stem within such an inflation valve.

BRIEF DESCRIPTION OF THE DRAWINGS

Some embodiments of the disclosure may be understood by referring, in part, to the following description and the accompanying drawings, wherein like reference numbers indicate like features, and wherein.

DETAILED DESCRIPTION

Specific example embodiments of the present disclosure are best understood by reference to FIGS. 1 through 4, wherein like numbers are used to indicate like and corresponding parts.

Figures 1, 2:
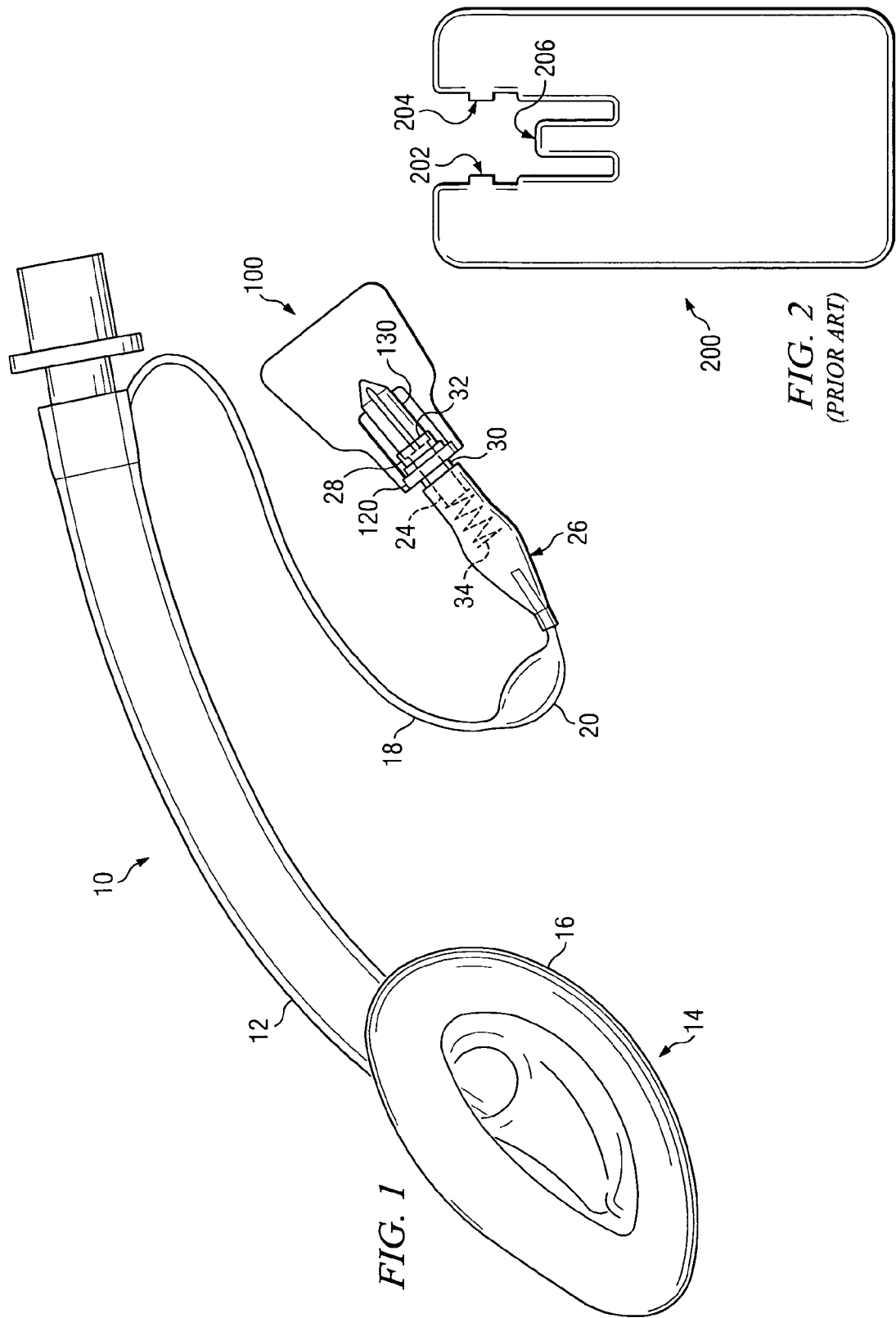
FIG. 1 illustrates a laryngeal mask in accordance with a specific example embodiment of the disclosure.
FIG. 2 illustrates a prior art vent clip.

Now referring to FIG. 1, a laryngeal mask, indicated generally at 10, is shown. Laryngeal mask 10 may include airway conduit 12 connected with mask 14. Mask 14 may include an inflatable portion 16. The inflatable portion 16 may be an inflatable cuff. After proper insertion into a subject, inflatable cuff 16 may be inflated to form a seal around a laryngeal inlet. Inflatable portion 16 is in fluid communication with inflation conduit 18 which may inflate inflatable cuff 16.

Inflation conduit 18 may be partially disposed within airway conduit 12. The inflation conduit 18 may also be provided outside of airway conduit 12 or may, e.g., be attached to an exterior surface of inflation conduit 12.

Laryngeal mask 10 may be provided as a single use product that is disposed of after use or may be a multiple use product that may be sterilized and reused. In one specific example embodiment, laryngeal mask 10 may comprise a single use Mallinckrodt LaryngoSeal® airway product. Laryngeal mask 10 may be constructed of polyvinyl chloride (PVC) or any other suitable material.

A pilot balloon 20 may be in fluid communication with inflation conduit 18 and with inflation valve 26. Inflation valve 26 may include an exterior housing 28 including an exit aperture 32. Inflation valve 26 may also include a movable valve stem 24, which may be operable between an open position allowing fluid communication with exit aperture 32 and a closed position closing off fluid communication with exit aperture 32. Valve stem 24 may be biased into a closed position by spring 34. In the present example embodiment, exterior housing 28 may have a generally cylindrical configuration. In alternative specific example embodiments, exterior housing 28 may have a non-cylindrical configuration. In the present example embodiment, exterior housing 28 may include groove 30, e.g., formed on the exterior surface thereof. Groove 30 may be a circumferential groove or may be formed partially around the exterior surface of exterior housing 28 and sized to interface with curved band 120 of vent clip 100 as discussed below. Vent clip 100 may be removably coupled to inflation valve 26. While removably coupled to inflation valve 26, valve stem 24 may be urged into an open position such that exit aperture 32 may be in fluid communication with inflation valve 26. Vent clip 100 may be constructed from polycarbonate or any other suitable material.

In operation after manufacture, vent clip 100 may be attached to inflation valve 26, e.g., to insure that valve stem 24 may be maintained in an open position. Vent clip 100 may remain attached to inflation valve 26 during sterilization processes as well as during packaging, shipment and/or storage. Prior to use on a subject, vent clip 100 may be removed from inflation valve 26 by grasping body portion 110 of vent clip 100 and then removing vent clip 100 from inflation valve 26.

Now referring to FIG. 2, which shows a prior art vent clip indicated generally as 200. As shown, prior art vent clip 200 includes a first gripping surface 202 and a second gripping surface 204, which extend from the prior art vent clip 200 and are provided to grip a small portion of the exterior surface of an inflation valve (not shown). Prior art vent clip 200 also includes projection 206, which may project into the interior of an inflation valve to depress a movable valve stem. As shown, prior art vent clip 200 provides minimal gripping surface with first gripping surface 202 and second gripping surface 204. In particular, the total gripping surface provided by first and second gripping surfaces 202 and 204 of prior art vent clip 200 typically interfaces with less than a 40° arc around the circumference of the exterior housing 28 of inflation valve 26.

Figure 3:
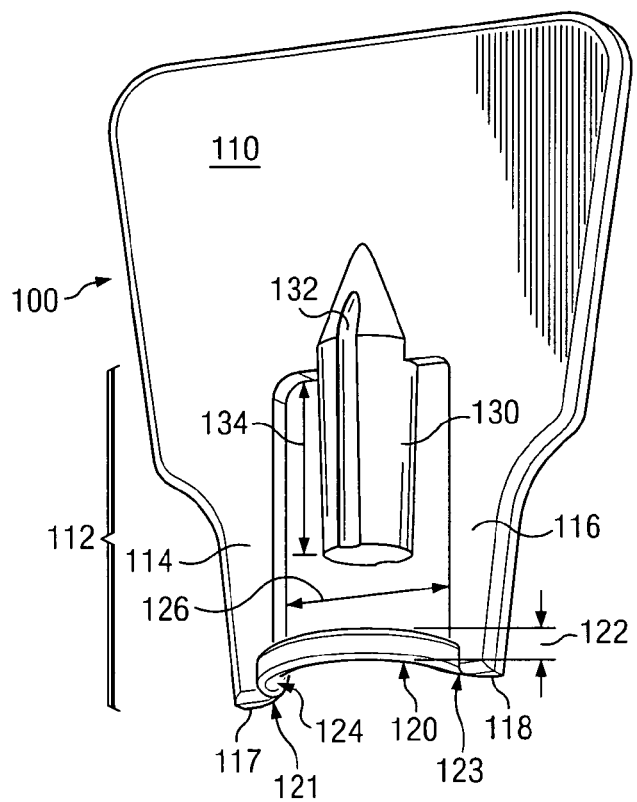
FIG. 3 illustrates a first view of a laryngeal mask vent clip according to a specific example embodiment of the disclosure.

Now referring to FIG. 3, vent clip 100 is shown. Vent clip 100 may include body portion 110 and exterior housing interface portion 112, which extends from body portion 110. Additionally, finger 130 may also extend from body portion 110.

Exterior housing interface portion 112 may include first member 114 and second member 116. First member 114 may include first member end 117 and second member 116 may include second member end 118. Curved band 120 may extend between first member end 117 and second member end 118. In particular, a first end 121 of curved band 120 may extend from first member end 117 and second end 123 of curved band 120 may extend from second member end 118. Curved band 120 may include an interior surface 124, which may provide a gripping surface with respect to an inflation valve 26 exterior housing 28. Additionally, curved band 120 may have a thickness 122. In a particular embodiment, thickness 122 may be provided in order to correspond with a groove 30 provided on the exterior housing 28 of an inflation valve 26 as shown in FIG. 1. In the present embodiment, curved band 120 may have a semi-circular configuration. In alternate embodiments, curved band 120 may also have a shape to correspond with the shape of the exterior housing 28 of an inflation valve 26. In particular, curved band 120 may have a non-semicircular shaped form to correspond with an exterior surface of a non-cylindrical exterior housing. In such embodiments, the terms "at least approximately 90 degree portion" or "an approximately 180 degree portion" may be interpreted to mean that at least 25 percent of a cross sectional area and approximately 50 percent of a cross sectional area, respectively.

In the present specific example embodiment, first member 114 and second member 116 may be provided in approximately the same plane and may extend in a generally parallel direction from body portion 110, offset by an offset distance 126. Offset distance 126 may be slightly larger than the exterior diameter of exterior housing 26 of inflation value 26. Additionally, curved band 120 may provide an approximately 180 degree semi-circle between first member 114 and second member 116. In alternate embodiments, curved band 120 may have a curved, but not semi-circular, shape. Additionally, first member 114 and second member 116 may be provided such that they are not on a common plane but are offset such that curved band 120 forms at least a 90 degree portion of a circle.

Body portion 110 may include an ergonomic design to facilitate thumb and forefinger manipulation with smooth corners to allow for intuitive installation and removal of vent clip 100 from inflation valve 26.

In the present embodiment, finger 130 may have a cylindrical configuration. Additionally, finger 130 may have a longitudinal groove 132 formed therein. Groove 132 may be be positioned along finger 130 to allow airflow in and out from the airway once valve stem 24 is in an open position. Finger 130 may be sized to engage the movable valve stem 24 and may have finger length 132 that may allow movable valve stem 24 to be urged into an open position when vent clip 100 is attached to inflation valve 26. Body portion 110 may also include text portion 136 formed therein.

Figure 4:
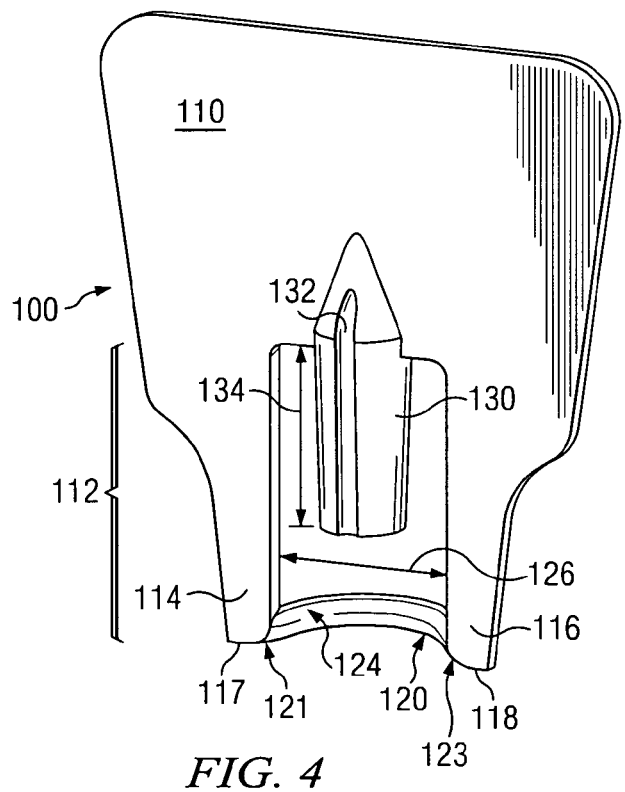
FIG. 4 illustrates a second view of a laryngeal mask vent clip according to a specific example embodiment of the disclosure.

Now referring to FIG. 4, a backside view of vent clip 100 is shown. As described in FIG. 3, vent clip 100 may include body portion 110 with an exterior housing interface portion 112 extending therefrom as well as finger 130 extending therefrom. Exterior housing interface portion 112 may include first member 114 and second member 116 as well as curved band 120 connected thereto. Curved band 120 may include gripping surface 124, which may provide, in the present embodiment, an approximately semi-circular surface for interfacing or engaging the exterior housing 28 of an inflation valve 26 as shown in FIG. 1. Finger 130 may include a longitudinal groove 132 formed therein and may have finger length 134.

First member 114 may be offset from second member 116 by offset distance 126. First member 114 may include first member end 117 and second member 116 may include second member end 118.

Although the disclosed specific example embodiments have been described in detail, it should be understood that various changes, substitutions and alterations can be made to the embodiments without departing from their spirit and scope. For instance, exterior housing 26 may have a non-cylindrical shape and may not include a grove 30 for interfering with a curved band 120 of a vent clip. Additionally, the curved band 120 of vent clip 100 may have a curved but non-circular shape and may have a thickness 122 greater or less than the thickness described. Additionally, first member 114 and second member 116 may be angularly offset such that curved band 120 spans at least a ninety (90) degree portion between first member 114 and second member 116. In another specific example embodiment, only a single member may be used to attach curved bands 120.

What is claimed is:
1. A laryngeal mask comprising:
an airway conduit;
a mask coupled to the airway conduit, the mask having an inflatable portion;
an inflation conduit associated with the inflatable portion of the mask;
an inflation valve in fluid communication with the inflation conduit, the inflation valve having an exterior housing with an exit aperture and a stem movable between an open position and a closed position; and a vent clip removably coupled to the inflation valve comprising:
 a body portion;
 an exterior housing interface portion extending from the body portion, the housing interface portion comprising a gripping surface formed to contact at least an approximately ninety degree portion of an exterior surface of the exterior housing; and
 a finger extending from the body portion generally along a longitudinal axis of the movable stem and sized to engage the movable stem within the inflation valve, wherein the finger maintains the stem in an open position when the vent clip is coupled to the inflation valve.

2. The laryngeal mask of claim 1, wherein the gripping surface is formed to contact at least an approximately one hundred eighty degree portion of the exterior housing.

3. The laryngeal mask of claim 1, wherein the exterior housing comprises a substantially cylindrical housing.

4. The laryngeal mask of claim 3, comprising a circumferential groove formed on an exterior surface of the generally cylindrical housing, the gripping surface sized to engage the circumferential groove.

5. The laryngeal mask of claim 1, wherein the housing interface portion comprises:
 a first member extending from the body portion;
 a second member extending from the body portion and offset from the first member; and
 a curved band having first and second ends, the first end connected to the first member and the second end connected to the second member, the curved band having an interior surface for providing the gripping surface.

6. The laryngeal mask of claim 5, wherein the curved band has an approximately semi-circular configuration.

7. The laryngeal mask of claim 1, wherein the inflation conduit runs on an interior portion of the airway conduit.

8. The laryngeal mask of claim 1, further comprising a pilot balloon coupled between the inflation conduit and the inflation valve.

9. The laryngeal mask of claim 1, wherein the finger has a substantially cylindrical configuration.

10. The laryngeal mask of claim 1, wherein the finger has a substantially longitudinal groove formed thereon.

11. The laryngeal mask of claim 10, wherein the finger has a length operable for urging the stem to an open position.

12. The laryngeal mask of claim 1, wherein the laryngeal mask is a single use laryngeal mask.

13. The laryngeal mask of claim 1, wherein the laryngeal mask is a multiple use laryngeal mask.

14. A vent clip for use with an inflation valve of a mask having an inflatable portion, the clip comprising:
 a body portion;
 an exterior housing interface portion extending from the body portion, the housing interface portion comprising a gripping surface formed to contact at least an approximately ninety degree portion of an exterior surface of an exterior housing of the inflation valve; and
 a finger extending from the body portion generally along a longitudinal axis of the movable stem and sized to engage a movable stem within the inflation valve wherein the finger maintains the movable stem in an open position when the vent clip is coupled to the inflation valve.

15. The vent clip of claim 14, wherein the gripping surface is formed to contact an approximately one hundred eighty degree portion of the exterior housing.

16. The vent clip of claim 14, wherein the gripping surface is sized to engage a circumferential groove formed in the exterior surface of the exterior housing.

17. The vent clip of claim 14, wherein the housing interface portion further comprises:
 a first member extending from the body portion;
 a second member extending from the body portion and offset from the first member; and
 a curved band having first and second ends, the first end connected to the first member and the second end connected to the second member, the curved band having an interior surface providing the gripping surface.

18. The vent clip of claim 17, wherein the curved band is a substantially semi-circular configuration.

19. The vent clip of claim 14, wherein the finger is substantially cylindrical.

20. The vent clip of claim 19, wherein the finger has a substantially longitudinal groove formed thereon.

21. The vent clip of claim 14, wherein the finger length is operable for urging the movable stem to an open position.

22. A method of making a laryngeal mask vent clip comprising the steps of:
 forming a vent clip body portion;
 forming an exterior housing interface portion extending from the body portion;
 forming a gripping surface for contacting at least an approximately ninety degree portion of an exterior surface of an exterior housing of a laryngeal mask inflation valve; and
 forming a finger extending from the body portion generally along a longitudinal axis of the movable stem and sized to engage a movable stem within the inflation valve and maintain the movable stem in an open position when the vent clip coupled to the inflation valve.

23. The method of claim 22, wherein forming the gripping surface comprises forming an approximately one hundred eighty degree portion of the exterior housing.

24. The method of claim 22, wherein forming the gripping surface comprises sizing the gripping surface to engage a circumferential groove formed in the exterior surface of the exterior housing.

25. The method of claim 22, wherein forming the exterior housing interface portion comprises:
 forming a first member extending from the body portion;
 forming a second member extending from the body portion and offset from the first member; and
 forming a curved band having first and a second ends, the first end connected to the first member and the second end connected to the second member, wherein the curved band has an interior surface for providing the gripping surface.

26. The method of claim 22, wherein forming the exterior housing interface portion comprises forming a curved band having a generally semi-circular configuration sized to contact the exterior surface of the exterior housing.

27. The method of claim 22, comprising removably coupling the vent clip to the laryngeal mask inflation valve wherein:
 the gripping surface contacts at least a ninety degree portion of an exterior surface of an exterior housing of the inflation valve; and
 the finger engages a movable stem within the inflation valve and urges the stem to an open position.

* * * * *